US012251321B2

(12) United States Patent
Davenport et al.

(10) Patent No.: US 12,251,321 B2
(45) Date of Patent: Mar. 18, 2025

(54) EXPANDABLE INTERVERTEBRAL IMPLANT

(71) Applicant: GLOBUS MEDICAL, INC., Audubon, PA (US)

(72) Inventors: Daniel Davenport, Collegeville, PA (US); Chad Glerum, Pennsburg, PA (US); Mark Weiman, Downingtown, PA (US); Duncan Sibson, Malvern, PA (US); Andrew Iott, Newtown Square, PA (US)

(73) Assignee: Globus Medical, Inc., Audubon, PA (US)

( * ) Notice: Subject to any disclaimer, the term of this patent is extended or adjusted under 35 U.S.C. 154(b) by 12 days.

(21) Appl. No.: 18/173,964

(22) Filed: Feb. 24, 2023

(65) Prior Publication Data
US 2023/0218406 A1 Jul. 13, 2023

Related U.S. Application Data

(63) Continuation of application No. 17/009,955, filed on Sep. 2, 2020, now Pat. No. 11,612,495, which is a
(Continued)

(51) Int. Cl.
*A61F 2/44* (2006.01)
*A61B 17/86* (2006.01)
*A61F 2/30* (2006.01)

(52) U.S. Cl.
CPC ............ *A61F 2/4455* (2013.01); *A61F 2/442* (2013.01); *A61B 17/86* (2013.01);
(Continued)

(58) Field of Classification Search
CPC .... A61F 2/44–4405; A61F 2/442–4425; A61F 2002/4415
See application file for complete search history.

(56) References Cited

U.S. PATENT DOCUMENTS

| 4,349,921 A | 9/1982 | Kuntz |
| 4,599,086 A | 7/1986 | Doty |

(Continued)

FOREIGN PATENT DOCUMENTS

| CA | 2088066 A1 | 1/1992 |
| DE | 4012622 C1 | 7/1991 |

(Continued)

OTHER PUBLICATIONS

U.S. Appl. No. 60/777,663, filed Feb. 27, 2006, Messerli.
(Continued)

*Primary Examiner* — Eduardo C Robert
*Assistant Examiner* — Steven J Cotroneo

(57) ABSTRACT

A joint spacer for therapeutically maintains separation of bones of a joint. A frame defines a longitudinal axis extending between distal and proximal ends. A carriage is slideably retained within the frame and has at least one ramped surface and a threaded portion. An actuator screw is threadably engaged with the threaded portion, and bears against said frame to cause the carriage to slideably move within the frame when the actuator screw is rotated. A first endplate engages a bone of the joint, and has at least one ramped surface that is mateable with the ramped surface of the carriage.

19 Claims, 4 Drawing Sheets

Related U.S. Application Data continuation of application No. 16/144,243, filed on Sep. 27, 2018, now Pat. No. 10,786,364, which is a continuation of application No. 13/775,731, filed on Feb. 25, 2013, now Pat. No. 10,117,754.

(52) U.S. Cl.
CPC ............... *A61F 2002/30507* (2013.01); *A61F 2002/30525* (2013.01); *A61F 2002/30556* (2013.01); *A61F 2002/30787* (2013.01); *A61F 2002/30904* (2013.01)

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,397,364 A | 3/1995 | Kozak et al. |
| 5,458,641 A | 10/1995 | Jiminez |
| 5,522,899 A | 6/1996 | Michelson |
| 5,534,030 A | 7/1996 | Navarro et al. |
| 5,549,612 A | 8/1996 | Yapp et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 5,861,041 A | 1/1999 | Tienboon |
| 5,888,223 A | 3/1999 | Bray, Jr. |
| 6,039,761 A | 3/2000 | Li et al. |
| 6,045,579 A | 4/2000 | Hochschuler et al. |
| 6,066,175 A | 5/2000 | Henderson et al. |
| 6,080,193 A | 6/2000 | Hochschuler et al. |
| 6,099,531 A | 8/2000 | Bonutti |
| 6,126,689 A | 10/2000 | Brett |
| 6,156,037 A | 12/2000 | LeHuec et al. |
| 6,176,882 B1 * | 1/2001 | Biedermann ............ A61F 2/447 623/17.11 |
| 6,200,347 B1 | 3/2001 | Anderson et al. |
| 6,206,922 B1 | 3/2001 | Zdeblick et al. |
| 6,231,610 B1 | 5/2001 | Geisler |
| 6,258,089 B1 | 7/2001 | Campbell et al. |
| 6,258,125 B1 | 7/2001 | Paul et al. |
| 6,383,186 B1 | 5/2002 | Michelson |
| 6,432,106 B1 | 8/2002 | Fraser |
| 6,482,233 B1 | 11/2002 | Aebi |
| 6,540,785 B1 | 4/2003 | Gill et al. |
| 6,558,423 B1 | 5/2003 | Michelson |
| 6,558,424 B2 | 5/2003 | Thalgott |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 * | 11/2003 | Wagner ................. A61F 2/4455 623/17.15 |
| 6,648,917 B2 | 11/2003 | Gerbec et al. |
| 6,666,889 B1 | 12/2003 | Commarmond |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,740,118 B2 | 5/2004 | Eisermann et al. |
| 6,752,832 B2 | 6/2004 | Ulrich |
| 6,814,756 B1 | 11/2004 | Michelson |
| 6,827,740 B1 | 12/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 6,899,735 B2 | 5/2005 | Coates et al. |
| 6,972,019 B2 | 12/2005 | Michelson |
| 7,001,432 B2 | 2/2006 | Keller et al. |
| 7,018,415 B1 | 3/2006 | McKay |
| 7,025,787 B2 | 4/2006 | Bryan et al. |
| 7,070,598 B2 | 7/2006 | Lim et al. |
| 7,137,997 B2 | 11/2006 | Paul |
| 7,147,665 B1 | 12/2006 | Bryan et al. |
| 7,153,325 B2 | 12/2006 | Kim et al. |
| 7,172,627 B2 | 2/2007 | Fiere et al. |
| 7,204,853 B2 | 4/2007 | Gordon |
| 7,217,291 B2 | 5/2007 | Zucherman et al. |
| 7,232,464 B2 | 6/2007 | Mathieu et al. |
| 7,276,082 B2 | 10/2007 | Zdeblick et al. |
| 7,282,063 B2 | 10/2007 | Cohen et al. |
| 7,309,357 B2 | 12/2007 | Kim |
| 7,316,714 B2 | 1/2008 | Gordon et al. |
| 7,320,708 B1 | 1/2008 | Bernstein |
| 7,473,276 B2 | 1/2009 | Aebi et al. |
| 7,547,325 B2 | 6/2009 | Biedermann et al. |
| 7,618,456 B2 | 11/2009 | Mathieu et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,771,475 B2 | 8/2010 | Michelson |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 7,875,078 B2 | 1/2011 | Wysocki et al. |
| 7,901,409 B2 | 3/2011 | Canaveral et al. |
| 7,909,869 B2 | 3/2011 | Gordon et al. |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,100,976 B2 | 1/2012 | Bray et al. |
| 8,105,382 B2 * | 1/2012 | Olmos ..................... A61F 2/447 623/17.15 |
| 8,123,810 B2 | 2/2012 | Gordon et al. |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,343,222 B2 | 1/2013 | Cope |
| 8,366,777 B2 * | 2/2013 | Matthis ................. A61F 2/4465 623/17.11 |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon et al. |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0010511 A1 | 1/2002 | Michelson |
| 2002/0016595 A1 | 2/2002 | Michelson |
| 2002/0045945 A1 | 4/2002 | Liu |
| 2002/0068976 A1 | 6/2002 | Jackson |
| 2002/0068977 A1 | 6/2002 | Jackson |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2003/0176926 A1 | 9/2003 | Boehm et al. |
| 2004/0030387 A1 | 2/2004 | Landry et al. |

(56) References Cited

U.S. PATENT DOCUMENTS

| | | |
|---|---|---|
| 2004/0049271 A1 | 3/2004 | Biedermann |
| 2004/0054412 A1 | 3/2004 | Gerbec et al. |
| 2004/0078078 A1 | 4/2004 | Shepard |
| 2004/0087947 A1 | 5/2004 | Lim et al. |
| 2004/0143270 A1 | 7/2004 | Zucherman et al. |
| 2004/0143332 A1 | 7/2004 | Krueger et al. |
| 2004/0153065 A1 | 8/2004 | Lim |
| 2004/0176853 A1 | 9/2004 | Sennett et al. |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0055098 A1 | 3/2005 | Zdeblick et al. |
| 2005/0065607 A1 | 3/2005 | Gross |
| 2005/0080422 A1 | 4/2005 | Otte et al. |
| 2005/0113916 A1 | 5/2005 | Branch |
| 2005/0149188 A1 | 7/2005 | Cook |
| 2005/0149192 A1 | 7/2005 | Zucherman et al. |
| 2005/0149193 A1 | 7/2005 | Zucherman et al. |
| 2005/0159819 A1 | 7/2005 | McCormack et al. |
| 2005/0171541 A1 | 8/2005 | Boehm |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0240267 A1 | 10/2005 | Randall et al. |
| 2005/0240271 A1 | 10/2005 | Zubok et al. |
| 2005/0251258 A1 | 11/2005 | Jackson |
| 2005/0256574 A1 | 11/2005 | Paul et al. |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0085071 A1 | 4/2006 | Lechmann et al. |
| 2006/0122701 A1 | 6/2006 | Kister |
| 2006/0129240 A1 | 6/2006 | Lessar et al. |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0217809 A1 | 9/2006 | Albert et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0088441 A1 | 4/2007 | Duggal et al. |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0191951 A1 | 8/2007 | Branch |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0255415 A1 | 11/2007 | Edie et al. |
| 2007/0270961 A1 | 11/2007 | Ferguson |
| 2007/0270963 A1 | 11/2007 | Melkent et al. |
| 2007/0270968 A1 | 11/2007 | Baynham |
| 2008/0021559 A1 | 1/2008 | Thramann |
| 2008/0051890 A1 | 2/2008 | Waugh et al. |
| 2008/0051907 A1 | 2/2008 | Marik |
| 2008/0065222 A1 | 3/2008 | Hamada |
| 2008/0114467 A1 | 5/2008 | Capote et al. |
| 2008/0133013 A1 | 6/2008 | Duggal et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac |
| 2008/0319487 A1 | 12/2008 | Fielding et al. |
| 2008/0319549 A1 | 12/2008 | Greenhalgh et al. |
| 2009/0024217 A1 | 1/2009 | Levy |
| 2009/0062833 A1 | 3/2009 | Song |
| 2009/0076608 A1 | 3/2009 | Gordon et al. |
| 2009/0076616 A1 | 3/2009 | Duggal et al. |
| 2009/0125062 A1 | 5/2009 | Uri |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0210062 A1* | 8/2009 | Thalgott ............... A61F 2/4465 606/301 |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza |
| 2009/0292361 A1 | 11/2009 | Lopez |
| 2009/0299478 A1 | 12/2009 | Carls et al. |
| 2009/0312763 A1 | 12/2009 | Mccormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1* | 8/2010 | Greenhalgh .......... A61F 2/4425 623/17.15 |
| 2010/0222816 A1 | 9/2010 | Gabelberger et al. |
| 2010/0286783 A1 | 11/2010 | Lechmann et al. |
| 2010/0292796 A1* | 11/2010 | Greenhalgh ....... A61B 17/8858 623/17.11 |
| 2011/0035011 A1 | 2/2011 | Cain |
| 2011/0093074 A1* | 4/2011 | Glerum ................ A61F 2/447 623/17.16 |
| 2011/0160861 A1 | 6/2011 | Jimenez et al. |
| 2011/0172774 A1 | 7/2011 | Varela |
| 2011/0251691 A1* | 10/2011 | McLaughlin ......... A61F 2/4611 623/17.16 |
| 2011/0276142 A1 | 11/2011 | Niemiec et al. |
| 2011/0301713 A1 | 12/2011 | Theofilos |
| 2011/0319997 A1* | 12/2011 | Glerum ................... A61F 2/442 623/17.11 |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163682 A1* | 6/2014 | Iott ....................... A61F 2/4455 623/17.15 |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |

(56) References Cited

U.S. PATENT DOCUMENTS

| | | |
|---|---|---|
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2727003 A1 | 5/1996 |
| FR | 2794968 | 12/2000 |
| FR | 2794968 A1 | 12/2000 |
| JP | 2000-513263 | 10/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1997023175 A1 | 7/1997 |
| WO | 199942062 A1 | 8/1999 |
| WO | 1999042062 A1 | 8/1999 |
| WO | 199966867 A1 | 12/1999 |
| WO | 1999063914 A1 | 12/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2005007040 A1 | 1/2005 |
| WO | 2006045094 A2 | 4/2006 |
| WO | 2006047587 A2 | 5/2006 |
| WO | 2006113080 A2 | 10/2006 |
| WO | 2007098288 A2 | 8/2007 |
| WO | 2008014258 A2 | 1/2008 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

OTHER PUBLICATIONS

U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, U.S. Dept. of Health and Human Services, Food and Drug Administration (Jun. 12, 2007).
M. Spruit et al., The in vitro stabilizing effect of polyetheretherketone cages versus a titanium cage of similar design for anterior lumbar interbody fusion, 14(8) Eur. Spine J. 752, 752-758 (2005).
P. Schleicher et al., Biomechanical comparison of two different concepts for stand alone anterior lumbar interbody fusion, 17(12) Eur. Spine J. 1757, 1757-1765 (2008).
P.W. Pavlov et al., Anterior lumbar interbody fusion with threaded fusion cages and autologous bone grafts, 9 Eur. Spine J. 224, 224-229 (2000).
Synthes' SynFix Technique Guide device ("SynFix Technique Guide").

* cited by examiner

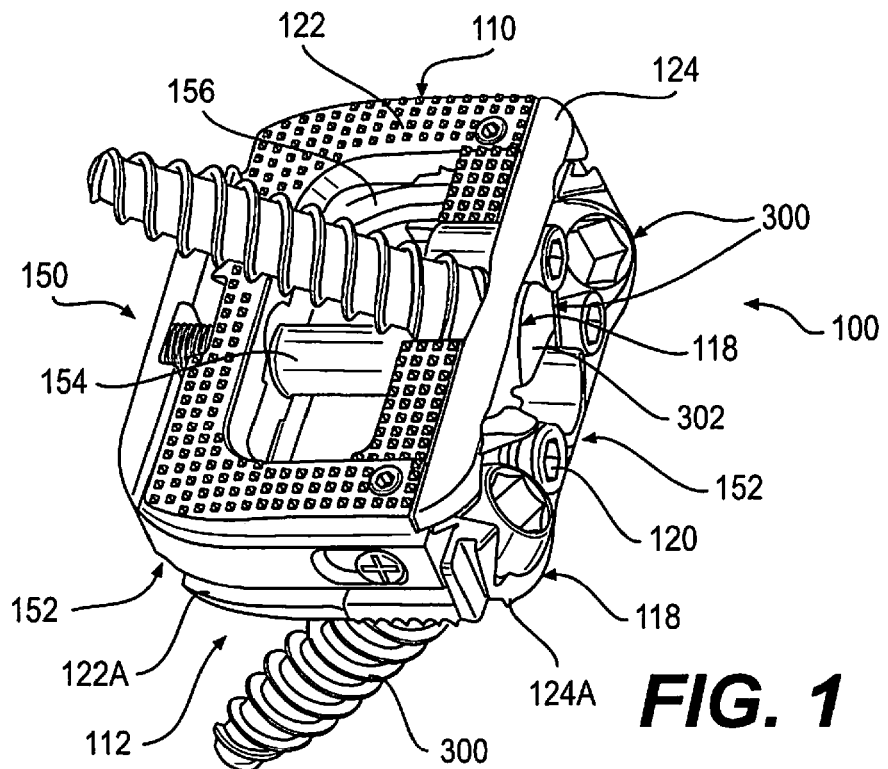
FIG. 1
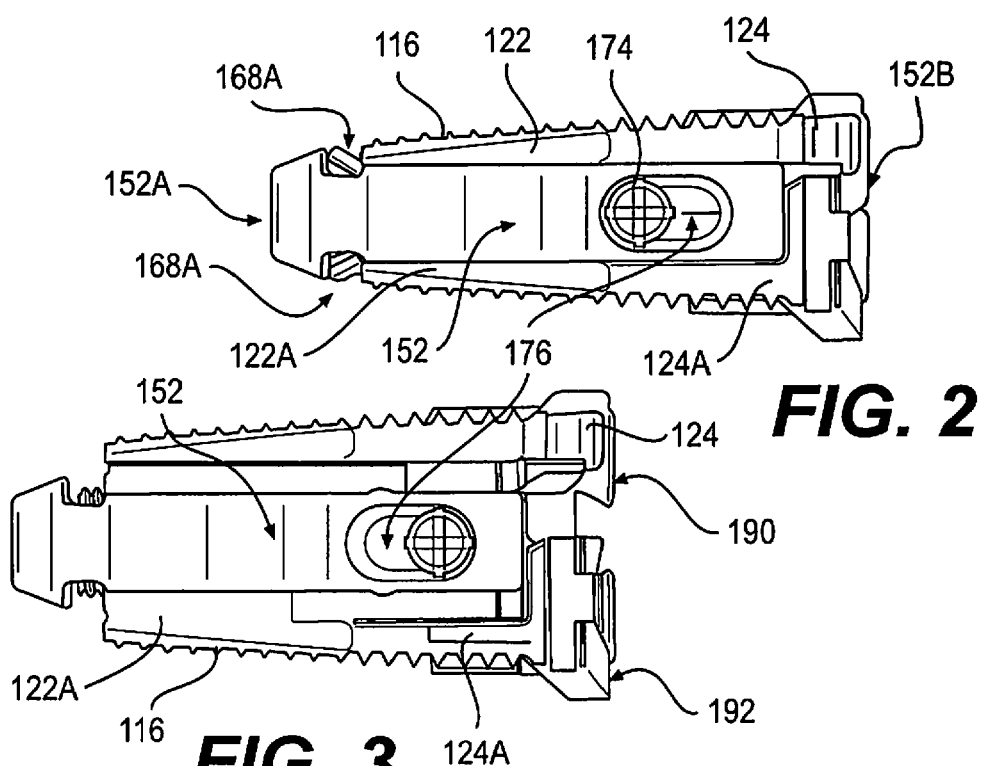
FIG. 2
FIG. 3

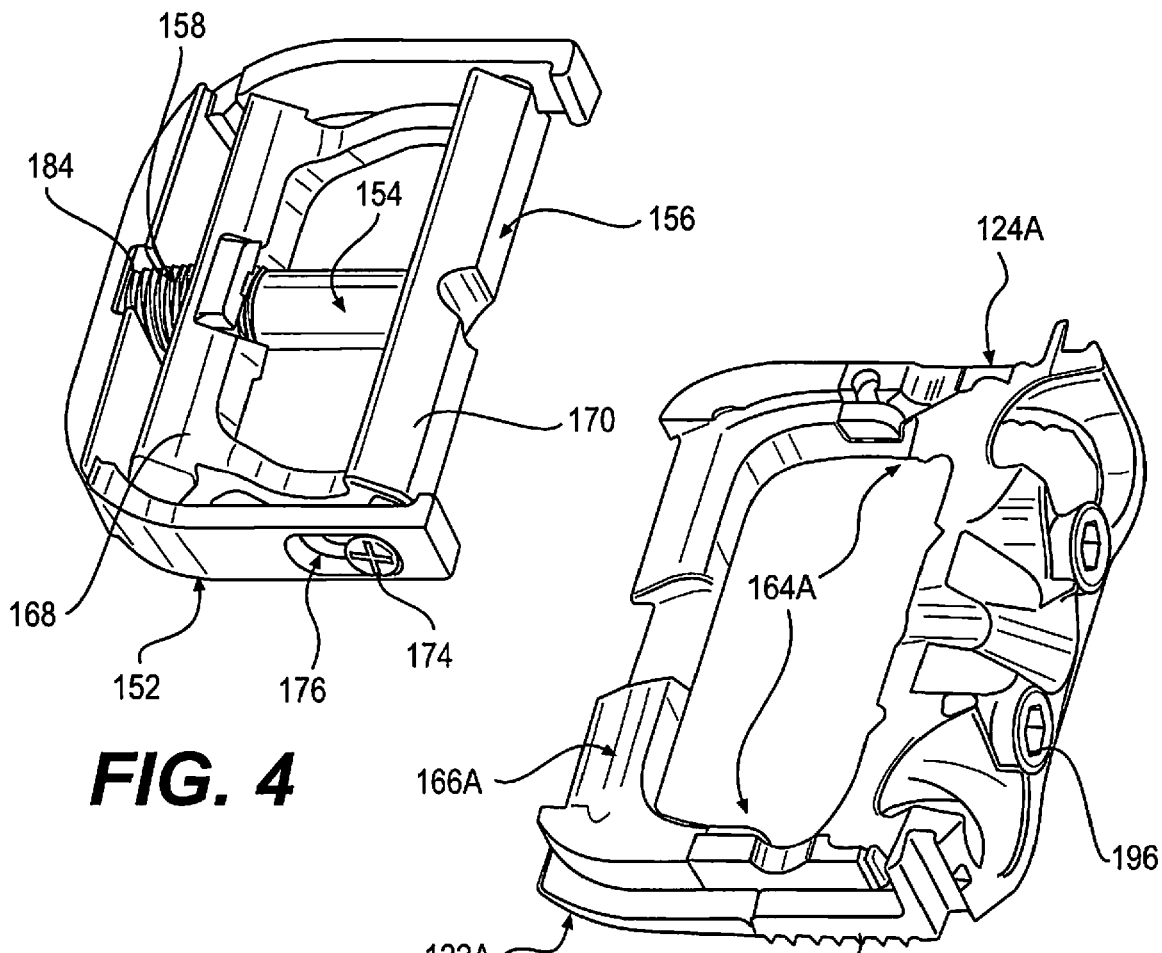
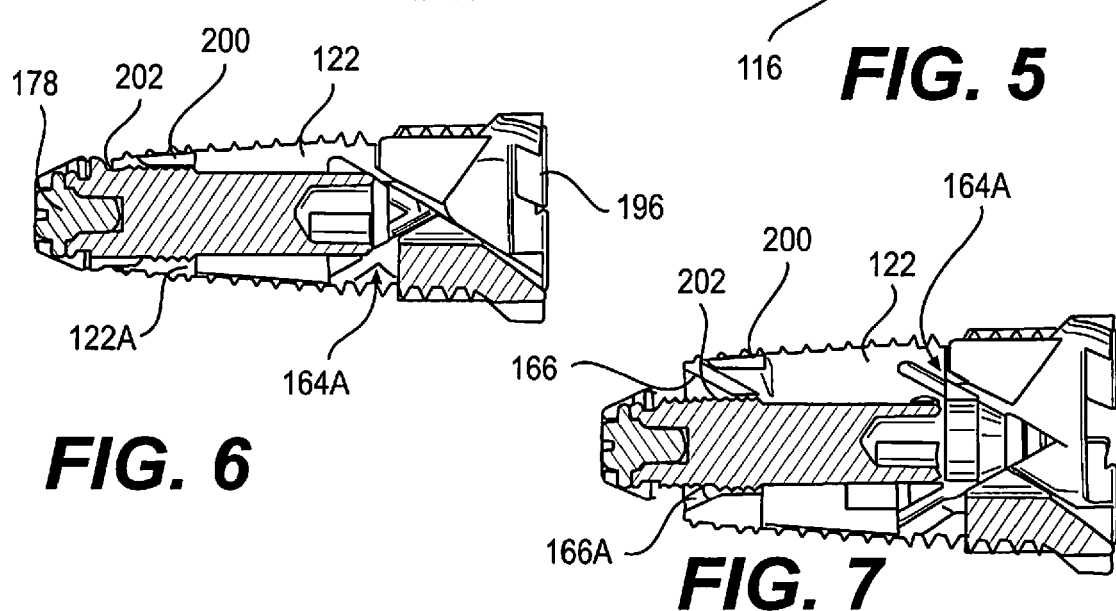

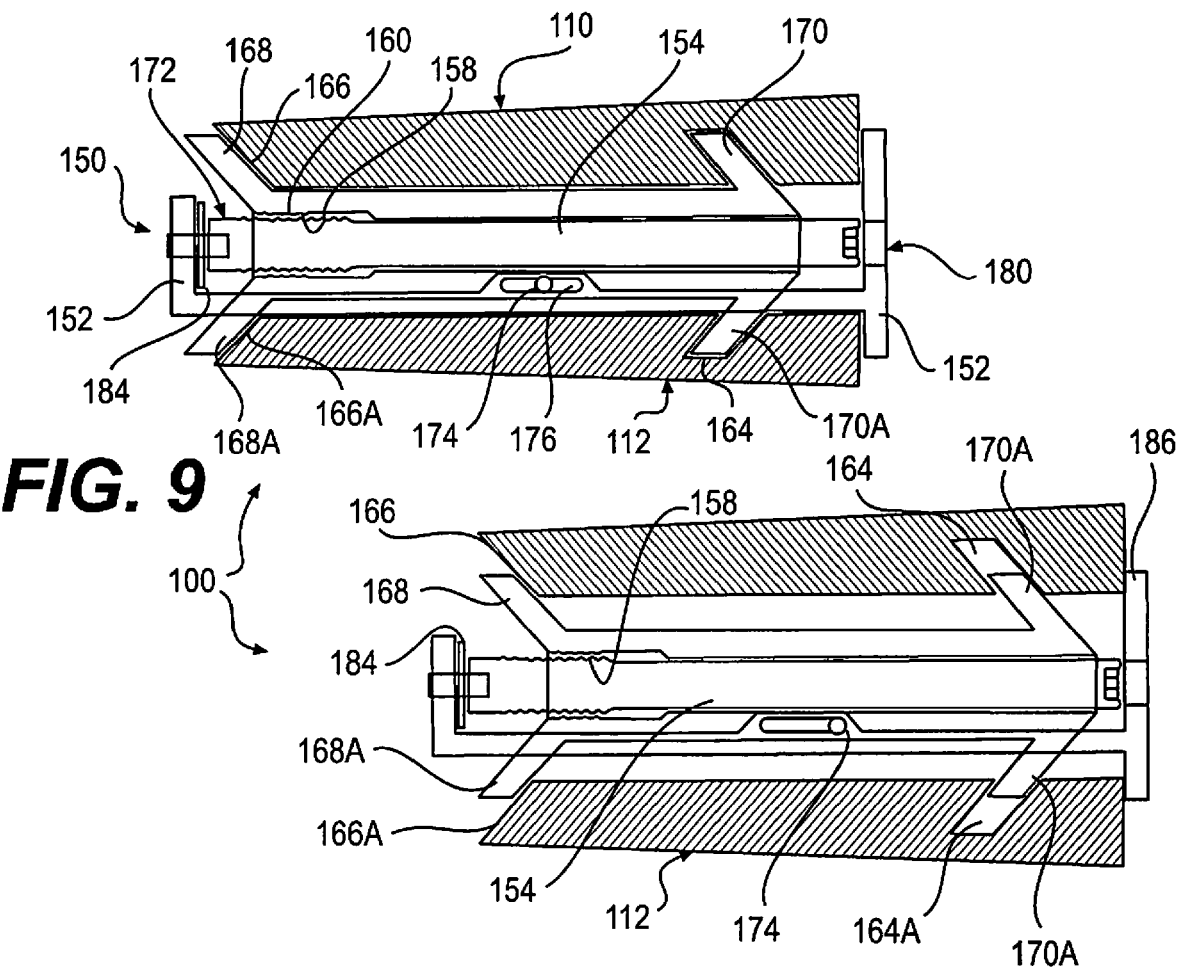
FIG. 9
FIG. 10
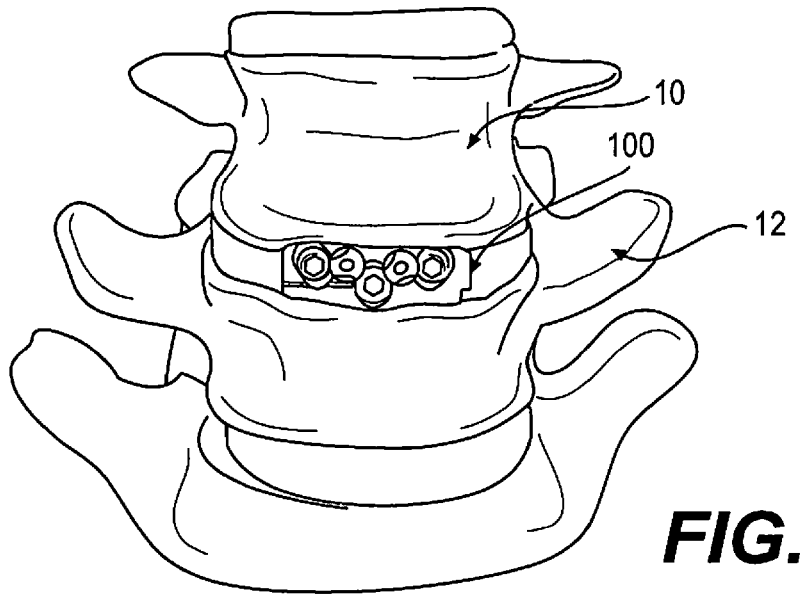
FIG. 11

EXPANDABLE INTERVERTEBRAL IMPLANT

CROSS-REFERENCE TO RELATED APPLICATIONS

The present application is a continuation of U.S. patent application Ser. No. 17/009,955 filed on Sep. 2, 2020, which is a continuation application of U.S. Ser. No. 16/144,243, filed on Sep. 27, 2018 (published as U.S. Pat. Pub. No. 2019-0021876), which is a continuation application of U.S. patent application Ser. No. 13/775,731, filed Feb. 25, 2013 (now U.S. Pat. No. 10,117,754), the entire contents of which is hereby incorporated by reference in its entirety.

FIELD OF THE INVENTION

This invention relates to stabilizing adjacent vertebrae of the spine by inserting an intervertebral spacer, and more particularly an intervertebral spacer that is adjustable in height.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY OF THE INVENTION

In accordance with the disclosure, a joint spacer for therapeutically maintaining a separation of bones of a joint, comprises: a frame having distal and proximal ends defining a longitudinal axis extending therebetween; a carriage slideably retained within the frame and having at least one ramped surface, the carriage further including a threaded portion; an actuator screw threadably engaged with the carriage threaded portion, the actuator screw configured to bear against the frame to cause the carriage to slideably move within the frame when the actuator screw is rotated; a first endplate configured to engage a first bone of the joint, and having at least one ramped surface mateable with the at least one carriage ramped surface, whereby when the carriage is slideably moveable by rotation of the actuator screw, the at least one endplate ramped surface slideable against the at least one carriage ramped surface to cause the first endplate to move along an axis transverse to the longitudinal axis to increase a height of the spacer; and a second endplate configured to engage a second bone of the joint.

In an embodiment thereof, the carriage includes at least one additional ramped surface, and the second endplate includes at least one ramped surface mateable with the at least one additional ramped surface of the carriage, whereby when the carriage is slideably moved by rotation of the actuator screw, the at least one second endplate ramped surface slides against the at least one additional carriage ramped surface to cause the second endplate to move along an axis transverse to the longitudinal axis to increase a height of the spacer.

In other embodiments thereof, the first endplate is configured to abut the frame as the first endplate is moved along an axis transverse to the longitudinal axis, whereby the first endplate moves substantially only along an axis transverse to the longitudinal axis; the first endplate includes at least one aperture through which a fastener may pass to secure the first endplate to a bone of the joint; the spacer further including a blocking mechanism to prevent backing out of a fastener passed through the first endplate; the first endplate includes one or more projections configured to engage bone of the joint when the implant is positioned between bones of the joint; at least one of the first and second endplates is composed of two interconnected portions of dissimilar materials; where dissimilar materials are used, one is metallic and includes at least one aperture through which a fastener may be passed to attach the implant to a bone of the joint. In another embodiment, one dissimilar material is polymeric, and another dissimilar material is metallic.

In further embodiments thereof, the carriage is slideably supported by the actuator screw and by at least one lateral support extending from the carriage to the frame; the spacer further includes a thrust washer interposed between the actuator screw and the frame; the spacer further includes a polymeric material configured to press against the actuator screw to reduce a potential for unintended rotation of the actuator screw.

In yet further embodiments, an aperture is formed in part by the first endplate, and in part by the second endplate, the aperture sized and dimensioned to rotatably support a bone screw when the first endplate has been moved a distance along the axis transverse to the longitudinal axis. In another embodiment, the spacer further includes a dovetail connection formed between the frame and the first endplate when the first endplate is configured to abut against the frame.

In another embodiment of the disclosure, a joint spacer for therapeutically maintaining a separation of bones of a joint, comprises a frame having distal and proximal ends defining a longitudinal axis extending therebetween; a carriage slideably retained within the frame and having at least one ramped surface, the carriage further including a threaded bore; an actuator screw threadably engaged with the carriage threaded bore, the actuator screw configured to bear against the frame to cause the carriage to slideably move within the frame when the actuator screw is rotated; a first endplate configured to engage a first bone of the joint, and having at least one channel having a ramped surface mateable with the at least one carriage ramped surface, whereby when the carriage is slideably moveable by rotation of the actuator screw in a first direction, the at least one endplate ramped surface slideable against the at least one carriage ramped surface to cause the first endplate to move along an axis transverse to the longitudinal axis to increase a height of the spacer; and a second endplate configured to engage a second bone of the joint.

In embodiments thereof, when the actuator screw is rotated in an opposite, second direction, the at least one endplate ramped surface is slideable against the at least one carriage ramped surface to cause the first endplate to move along an axis transverse to the longitudinal axis to decrease a height of the spacer; and, the carriage is slideably supported by the actuator screw and by at least one screw extending from the carriage through an elongated channel in the frame.

In yet further embodiments thereof, the first endplate includes a metallic portion having an aperture through which a fastener may be passed for connecting the implant to body tissue, the first endplate further having a polymeric portion connected to the metallic portion, the polymeric portion sized and dimensioned to support a bone of the joint; and, the frame and the first endplate include mateable dovetailed portions configured to maintain an orientation of the first endplate and the frame when the first endplate is positioned proximate the frame.

In another embodiment of the disclosure, a method for therapeutically maintaining a separation of bones of a joint, comprises: inserting a spacer between bones of the joint, the spacer including—a frame having distal and proximal ends defining a longitudinal axis extending therebetween; a carriage slideably retained within the frame and having at least one ramped surface, the carriage further including a threaded bore; an actuator screw threadably engaged with the carriage threaded bore, the actuator screw configured to bear against the frame to cause the carriage to slideably move within the frame when the actuator screw is rotated; a first endplate configured to engage a first bone of the joint, and having at least one ramped surface mateable with the at least one carriage ramped surface, whereby when the carriage is slideably moveable by rotation of the actuator screw, the at least one endplate ramped surface slideable against the at least one carriage ramped surface to cause the first endplate to move along an axis transverse to the longitudinal axis to increase a height of the spacer; and a second endplate configured to engage a second bone of the joint; the spacer inserted when the first endplate is positioned proximate the frame; and slideably moving, by rotation of the actuator screw, the at least one endplate ramped surface against the at least one carriage ramped surface to cause the first endplate to move along an axis transverse to the longitudinal axis to increase a height of the spacer to maintain a separation of bones of the joint.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIG. 1 depicts a spacer of the disclosure, together with three mounted bone screws;

FIG. 2 depicts the spacer of FIG. 1, in a compressed or reduced height configuration;

FIG. 3 depicts the spacer of FIG. 1, in an expanded or increased height configuration;

FIG. 4 depicts a carriage and frame of the spacer of FIG. 1;

FIG. 5 depicts an endplate of the spacer of FIG. 1;

FIG. 6 depicts a cross-section of the spacer of FIG. 2;

FIG. 7 depicts a cross-section of the spacer of FIG. 3;

FIG. 9 depicts a diagrammatic view of aspects of a spacer in accordance with the disclosure, in a reduced height configuration;

FIG. 10 depicts a the spacer of FIG. 9, in an expanded height configuration; and FIG. 11 depicts the spacer of FIG. 1, implanted between adjacent vertebrae.

DETAILED DESCRIPTION OF THE INVENTION

Figure 8:
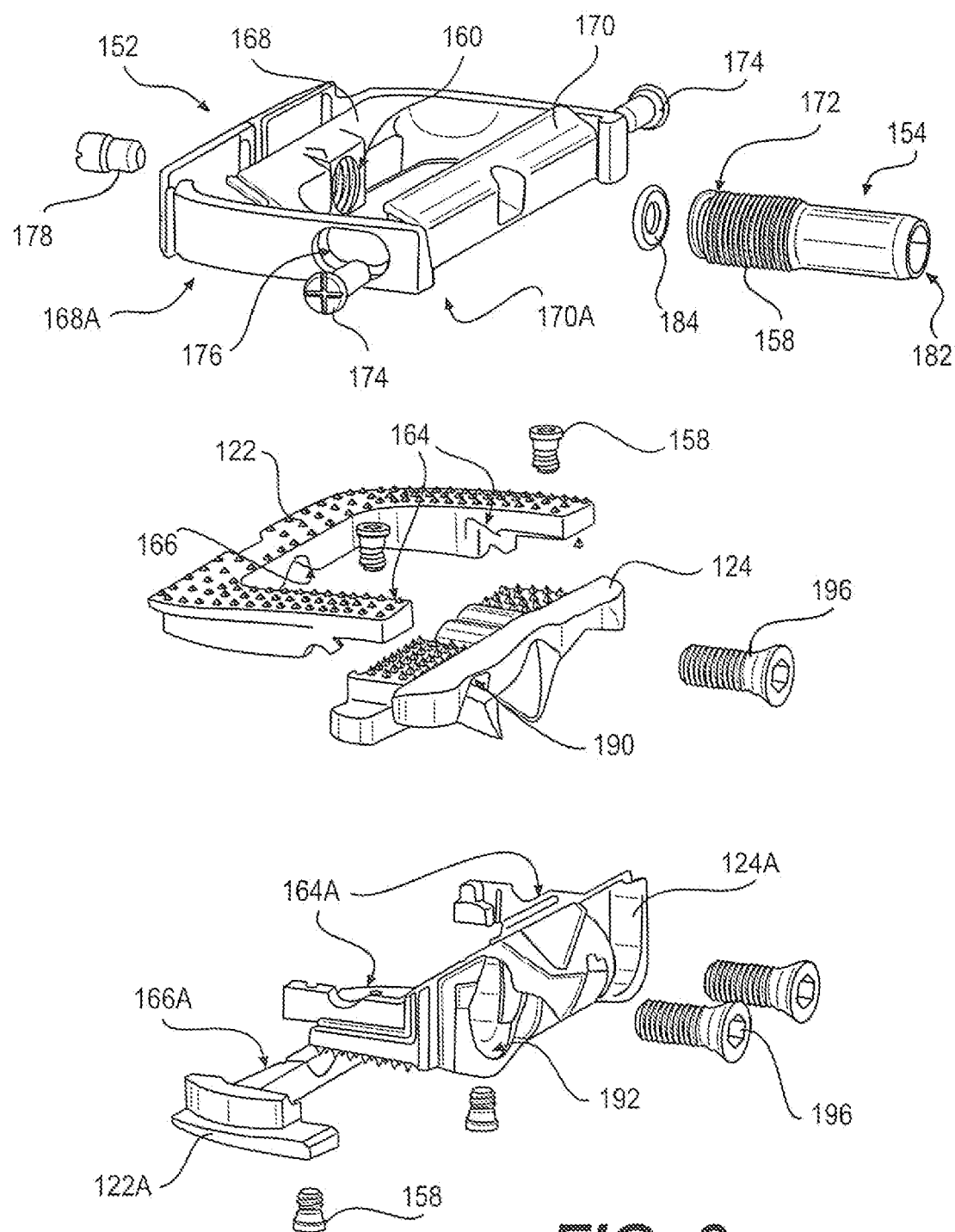
FIG. 8 depicts an exploded view of the spacer of FIG. 1.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

With reference to FIGS. 1-3, implant 100 is operative, when positioned between adjacent bones of a joint, such as for example vertebrae 10, 12 (shown in FIG. 11), to stabilize a joint formed by adjacent vertebrae. Implant 100 has a collapsed state or height, illustrated in FIG. 2, and an expanded state or height, illustrated in FIG. 3. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed stated, implants 100 reduce impaction to tissue in the joint space during insertion, and form the least visually blocking or obstructing profile.

Implant 100 includes two separable endplates 110, 112. A surface 114 of an endplate 110, 112 can be provided with teeth or other projections 116 which can penetrate body tissue to reduce a likelihood of migration of implant 100 after implantation. Implant 100 is further secured with one or more bone screws 300, which pass through bone screw socket 118 within implant 100, and into body tissue of the patient. In the embodiment illustrated in FIGS. 1-3, three sockets 118 for three bone screws are provided, the bone screws 300 further retained in connection with implant 100 by blocking fasteners 120. Bone screw 300 can be a polyaxial screw, and sockets 118 correspondingly shaped, whereby bone screw 300 may be inserted into body tissue at an optimal angle with respect to implant 100, whereby optimal purchase may be obtained, or certain body tissue may be avoided.

Endplates 110, 112 are moveably connectable to an actuator 150 operable to change a relative relationship of endplates 110 and 112. Actuator 150 includes a frame 152 rotatably supporting an actuator screw 154, and a moveable carriage 156. As actuator screw 154 rotates within frame 152, carriage 156 slides within frame 152, driven by cooperation between threads 158 (FIG. 8) upon actuator screw 152, and mating threads 160 within carriage 156. In the embodiment of FIGS. 1-3, endplates 110 and 112 are formed in two connected portions, including a portion 122, 122A which can be polymeric, and a portion 124, 124A, which can be metallic. The portions are joined in the embodiment shown by screws 162, although other methods of combining the two connected portions 122, 124 or 122A and 124A may be used, including a dovetail connection, or adhesive, possibly in combination with each other, or with endplate connector screws 162. Metallic portions 124, 124A can provide greater strength for portions of implant 100 which are under relatively greater stress, for example portions through which a fastener may pass to anchor implant 100 within the body. While portions 122, 122A, 124, 124A are described as polymeric or metallic, it should be understood that other materials may be used, and that the portions can be of dissimilar materials.

With reference to FIG. 2, it may be seen that implant 100 is in a compressed state, having a lower height relative to an expanded state, as shown in FIG. 3. A functioning of device 100 may be best understood with reference to FIGS. 9-10, which correlate with FIGS. 2-3, respectively, but which present a simplified view having certain elements eliminated or exaggerated, to ease understanding. Endplates 110 and 112 are provided with ramped channels 164, 164A, and an open ramp 166, 166A, sized to slidingly receive ramps 168, 168A and 170, 170A disposed upon carriage 156. While two mating channels and ramps are illustrated for each endplate 110, 120, it should be understood that one, or more than two, sets of channels and or ramps may be provided. Further, channels 164, 164A may alternatively be formed as ramps. However, a channel can operate to enable a reduction of height, having an opposing ramp face, whereby rotation of actuator screw 152 in an opposite direction to expansion can drive endplates 110, 112 together, for example when pressure from body tissue is insufficient to collapse endplates 110, 112. Additionally, at least one channel can operate to foster the maintenance of a connection between carriage 156 and an endplate 110, 112.

Carriage 156 is supported by frame 152 by lateral engagement means, in this embodiment two support screws 174 engaged with carriage 156, and passable through respective channels 176 formed in frame 152. Distal end 172 of actuator screw 154 provides additional support for carriage 156. Actuator screw 154 is supported by a set screw 178, which passes through and is rotatably supported within frame 152.

An actuator access port 180 permits passage of a tool, for example a hex driver (not shown), into engagement with a proximal end 182 of actuator screw 152. As actuator screw 152 is turned, distal end 172 bears against a thrust washer 184, and an end portion of frame 152. As actuator screw 152, carriage 156 is driven along actuator screw by interaction of threads 158 and 160. As carriage 156 moves, endplates 110, 112 are urged to move along ramps 168, 168A and 170, 170A, moving relatively apart, and increasing a height of spacer 100. Endplates 110, 112 are prevented from moving together with carriage 156 by abutting against an end portion 186 of frame 152. In a given orientation, one of endplate 110 and 112 is an upper endplate with respect to an orientation in a standing patient. However, implant 100 may, in some embodiments, be implantable in either of opposite orientations, and therefore designations of upper and lower are provided for ease of understanding, only. It should be understood that only one of endplate 110, 112 may be moveable with respect to the other. For example, in one embodiment, ramps 168A, 170A may not be provided, and endplate 112 may be attached to frame 152.

FIG. 11 illustrates a spacer 100 of the disclosure implanted between adjacent vertebrae 10, 12. Frame 152 defines a distal or leading end 152A which is inserted first into the body, and a proximal or trailing end 152B which passes last into the body, the distal and proximal ends defining a longitudinal axis extending therebetween. Spacer 100 can be inserted into the body, and into a position between vertebrae, using minimally invasive methods, for example using a small incision, and spacer 100 may be passed through a cannula or other structure which maintains a pathway through body tissue. Spacer 100 may be inserted into the spinal column through any approach, including anterior, anterolateral, lateral, or posterolateral. A portion of the disc annulus, and nucleus pulposus may be removed in order to form a space into which spacer 100 may be inserted. When spacer 100 is in a compressed, or reduced height configuration, dovetail guides 200, 202 can be provided to foster maintenance of a relative orientation of upper and lower endplates during insertion or removal of device 100.

Spacer 100 can be inserted configured to have a lower height profile, as shown in FIG. 2, whereby an extent of distraction of body tissue may be reduced during insertion. Moreover, to the extent that spacer 100 is used to open a pathway towards an implantation site, trauma to adjacent tissue is reduced relative to inserting a spacer having a final height profile. Once spacer 100 is positioned between adjacent vertebrae, actuator screw is rotated by a tool. The tool may be positioned entirely within the body, or can extend from in interior of the body to outside the body, for example having a driving tip at one end and having a handle at an opposite end, with a shaft extending into the body between each end.

Once actuator screw 154 has been rotated to separate endplates 110, 112 a desired amount, the tool is removed. At this point, actuator screw 154 may be secured in place, for example using a mechanical block, or an adhesive, to prevent unintended rotation of actuator screw 154. As carriage 156 is slideably moved by rotation of actuator screw 154, a ramp 166, 166A or a ramped surface of channel 164, 164A of at least one of endplate 110, 112 slides against at least one ramp 168, 168A, 170, or 170A of carriage 156, to cause the endplate to move along an axis transverse to the longitudinal axis of the frame, to increase a height of the spacer. Rotation of actuator screw 154 in an opposite direction causes movement along an axis transverse to the longitudinal axis of the frame to decrease a height of the spacer.

Polymeric insets, or a polymeric square nut, for example PEEK, can be provided, engageable with threads 158 or other portion of actuator screw 152, to provide additional friction to prevent height loss under load, particularly under cyclic loading. Similarly, once bone screws 300 have been inserted, blocking elements 196 may be rotated to extend over an end of bone screw head 302, preventing screw 300 from backing out. A similar mechanical block (not shown) may be provided for actuator screw 154.

With reference to FIGS. 1-3, 5-8, it may be seen that a socket 118 for a polyaxial screw head 302 can be formed entirely within one of upper or lower endplate 110, 112, or may be formed partially within each of endplate 110 and 112, whereby when spacer 100 has been expanded to a final height, the proportions of an interior of socket 118 are correct or substantially correct for retaining screw head 302. For example, in FIG. 8, metallic portion 124 forms an upper portion 190 of socket 118, and mating metallic portion 124A forms a lower portion 192 of socket 118. In the embodiment illustrated in the figures, there are three sockets 118, and all are formed of upper and lower portions. However, there may be more or fewer sockets 118, and one or more sockets may be formed entirely in an upper or lower endplate.

In an embodiment, spacer 100 of the disclosure provides an actuator that translates relative to the body by means of a threaded actuator screw 154. Ramps 168, 168A and 170, 170A on a carrier 152 mate with channels 164, 164A, and or ramps 166, on endplates 110, 112. Linear translation of carriage 152 causes endplates 110, 112 to expand implant 100 along an S/I axis with respect to the body. There can be dovetail guides that capture endplates 110, 112 when collapsing the implant.

Assembly screws 162 fasten endplates made of dissimilar materials, for example PEEK polymeric portions 122, 122A to Titanium metallic portions 124, 124A. A dovetail and press fit design can be used to connect the dissimilar endplate portions. A PEEK bushing or washer 184 is used between the threaded actuator screw 154 and frame 152 to minimize friction during expansion of implant 100. Support screws 174 and channels 176 cooperate to form side or lateral stabilizers, and set screw 178 supports a nose or leading end of carriage 152. Additionally, cooperating slots and projections (not shown) in carriage 156 and frame 152 can be provided for further relative guidance and stability.

In one embodiment, three bone screws 300 are used to provide fixation into adjacent vertebral bodies, two screws 300 passing through implant 100 and into one vertebra, and one screw 300 passing through implant 100 into another vertebra, although other combinations may be used. Bone screws 300 can have spherical or otherwise curved heads, facilitating insertion at a desired angle, or may be provided to mate with socket 118 in a fixed orientation, particularly depending on a diameter of a neck portion of screw 300. Cam style blocking fasteners 120 can be used to block bone screws 300 from backing out after being inserted.

Implants of the disclosure enable a continuous expansion and retraction over a range of displacements according to predetermined dimensions of a specific implant 100 design. This provides the ability to distract vertebral bodies to a desired height, but also to collapse the implant 100 for repositioning, if therapeutically advantageous for the patient. Endplates 110, 112 may be shaped to form planes or surfaces which converge relative to each, to provide for lordosis, and can be provided with openings through which bone may grow, and into which bone graft material may be placed. Implant 100 may be used to distract, or force bones of a joint apart, or may be used to maintain a separation of bones created by other means, for example a retractor.

Implant 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

For example, metallic portions 124, 124A of endplates 110, 112 may be manufactured from Titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Polymeric portions 122, 122A may be manufactured from ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of implant 100. For example, polymeric portions 122, 122A can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates 110, 112, to provide for a natural lordosis, or a corrective lordosis, for example of from 0° to 6° for a cervical application, although much different values may be advantageous for other joints. Lordotic angles may also be formed by shaping one or both of plates 110, 112 to have relatively non-coplanar surfaces. Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Implants 100 may be implanted within any level of the spine, and may also be implanted in other joints of the body, including joints of the hand, wrist, elbow, shoulder, hip, knee, ankle, or foot.

In accordance with the invention, a single implant 100 may be used, to provide stabilization for a weakened joint or joint portion. Alternatively, two, three, or more implants 100 may be used, at a single joint level, or in multiple joints. Moreover, implants 100 may be combined with other stabilizing means.

Additionally, implant 100 may be fabricated using material that biodegrades in the body during a therapeutically advantageous time interval, for example after sufficient bone ingrowth has taken place. Further, implant 100 is advantageously provided with smooth and or rounded exterior surfaces, which reduce a potential for deleterious mechanical effects on neighboring tissues.

Any surface or component of the invention may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to at the involved level. The surgery position implant 100 may be performed through an Anterior, Anterolateral, Posterolateral, and/or Lateral approach.

In a typical embodiment, implant 100 has a uncompressed height, before insertion, of 12 to 18 mm, and may advantageously be provided in cross-sections of 23×32 mm, 26×38 mm and 26×42 mm, with 4, 8, 12, or 16 degree lordotic angles, although these are only representative sizes, and substantially smaller or larger sizes can be therapeutically beneficial. In one embodiment a spacer 100 in accordance with the instant disclosure is sized to be inserted using an MIS approach (a reduced incision size, with fewer and shorter cuts through body tissue).

Implant 100 may advantageously be used in combination with other known or hereinafter developed forms of stabilization or fixation, including for example rods and plates.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A joint spacer for therapeutically maintaining a separation of bones of a joint, comprising:
   a frame having a first lateral side, a second lateral side, and distal and proximal ends, the distal and proximal ends defining a longitudinal axis extending therebetween, the first lateral side and the second lateral side defining a width of the frame;
   a carriage having a first lateral side, a second lateral side, and distal and proximal ends, the carriage slideably positionable within the frame, the carriage having at least one ramped surface and a threaded portion, the first lateral side of the carriage and the second lateral side of the carriage defining a width of the carriage, wherein the width of the carriage is approximate the width of the frame;
   an actuator screw threadably engaged with said carriage threaded portion, said actuator screw configured to bear against said frame to cause said carriage to slideably move within said frame when said actuator screw is rotated;
   a first endplate configured to engage a first bone of the joint, and having at least one ramped surface mateable with said at least one carriage ramped surface; and
   a second endplate configured to engage a second bone of the joint;
   wherein said carriage includes at least one additional ramped surface, and said second endplate includes at least one ramped surface mateable with said at least one additional ramped surface of said carriage,
   wherein when said carriage is slideably moved by rotation of said actuator screw, said at least one second endplate ramped surface slides against said at least one additional carriage ramped surface to cause said second endplate to move along an axis transverse to said longitudinal axis to increase a height of the spacer, and
   wherein the first endplate and the second endplate are capable of moving with respect to the frame.

2. The joint spacer of claim 1, said first endplate configured to abut said frame as said first endplate is moved along an axis transverse to said longitudinal axis, whereby said first endplate moves substantially only along an axis transverse to said longitudinal axis.

3. The joint spacer of claim 1, wherein said first endplate includes at least one aperture through which a fastener may pass to secure said first endplate to a bone of the joint.

4. The joint spacer of claim 3, further including a blocking mechanism to prevent backing out of a fastener passed through said first endplate.

5. The joint spacer of claim 1, wherein said first endplate includes one or more projections configured to engage bone of the joint when the implant is positioned between bones of the joint.

6. The joint spacer of claim 1, wherein at least one of said first and second endplates is composed of two interconnected portions of dissimilar materials.

7. The joint spacer of claim 6, wherein one of said dissimilar materials is metallic and includes at least one aperture through which a fastener may be passed to attach the implant to a bone of the joint.

8. The joint spacer of claim 6, wherein one dissimilar material is polymeric, and another dissimilar material is metallic.

9. The joint spacer of claim 1, wherein said carriage is slideably supported by said actuator screw and by at least one lateral support extending from said carriage to said frame.

10. The joint spacer of claim 1, further including a thrust washer interposed between said actuator screw and said frame.

11. The joint spacer of claim 1, further including a polymeric material configured to press against said actuator screw to reduce a potential for unintended rotation of said actuator screw.

12. The joint spacer of claim 1, further including an aperture formed in part by said first endplate, and in part by said second endplate, said aperture sized and dimensioned to rotatably support a bone screw when said first endplate has been moved a distance along the axis transverse to said longitudinal axis.

13. The joint spacer of claim 1, further including a dovetail connection formed between said frame and said first endplate when said first endplate is configured to abut against said frame.

14. The joint spacer of claim 1, wherein the spacer has a length between distal and proximal ends of the spacer along the longitudinal axis and a width between first and second sides of the spacer, wherein the width is greater than the length of the spacer.

15. A joint spacer for therapeutically maintaining a separation of bones of a joint, comprising:
   a frame having distal and proximal ends defining a central longitudinal axis extending therebetween;
   a carriage slideably positionable within the frame, the carriage having at least one ramped surface and a threaded bore, the threaded bore extending along the central longitudinal axis;
   an actuator screw extending along the central longitudinal axis and threadably engaged with said carriage threaded bore, said actuator screw configured to bear against said frame to cause said carriage to slideably move within said frame when said actuator screw is rotated;
   a first endplate configured to engage a first bone of the joint, and having at least one channel having a ramped surface mateable with said at least one carriage ramped surface, whereby when said carriage is slideably moveable by rotation of said actuator screw in a first direction, said at least one endplate ramped surface slideable against said at least one carriage ramped surface to cause said first endplate to move along an axis transverse to said longitudinal axis to increase a height of the spacer; and a second endplate configured to engage a second bone of the joint,
wherein the first endplate and the second endplate are capable of moving with respect to the frame.

16. The spacer of claim 15, wherein when said actuator screw is rotated in an opposite, second direction, said at least one endplate ramped surface is slideable against said at least one carriage ramped surface to cause said first endplate to move along an axis transverse to said longitudinal axis to decrease a height of the spacer.

17. The spacer of claim 15, wherein said carriage is slideably supported by said actuator screw and by at least one screw extending from said carriage through an elongated channel in said frame.

18. The spacer of claim 15, wherein said first endplate includes a metallic portion having an aperture through which a fastener may be passed for connecting the implant to body tissue, the first endplate further having a polymeric portion connected to said metallic portion, the polymeric portion sized and dimensioned to support a bone of the joint.

19. The spacer of claim 15, wherein said frame and said first endplate include mateable dovetailed portions configured to maintain an orientation of said first endplate and said frame when said first endplate is positioned proximate said frame.

* * * * *